(12) United States Patent
Liang et al.

(10) Patent No.: US 11,969,539 B2
(45) Date of Patent: Apr. 30, 2024

(54) MANIFOLD

(71) Applicant: AMSINO MEDICAL (SHANGHAI) CO., LTD., Shanghai (CN)

(72) Inventors: Hongqi Liang, Shanghai (CN); Richard Ya Lee, Shanghai (CN)

(73) Assignee: AMSINO MEDICAL (SHANGHAI) CO., LTD., Shanghai (CN)

( * ) Notice: Subject to any disclaimer, the term of this patent is extended or adjusted under 35 U.S.C. 154(b) by 363 days.

(21) Appl. No.: 17/423,581

(22) PCT Filed: Mar. 9, 2020

(86) PCT No.: PCT/CN2020/078376
§ 371 (c)(1),
(2) Date: Jul. 16, 2021

(87) PCT Pub. No.: WO2020/147865
PCT Pub. Date: Jul. 23, 2020

(65) Prior Publication Data
US 2022/0111136 A1    Apr. 14, 2022

(30) Foreign Application Priority Data

Jan. 16, 2019  (CN) .......................... 201910039560.0

(51) Int. Cl.
*A61M 1/00*       (2006.01)
*B01D 35/027*     (2006.01)
(Continued)

(52) U.S. Cl.
CPC ........... *A61M 1/743* (2021.05); *B01D 35/027* (2013.01); *F16L 29/02* (2013.01); *A61B 50/36* (2016.02);
(Continued)

(58) Field of Classification Search
CPC .... A61M 1/743; A61M 2205/75; A61M 1/78; A61M 1/784; A61M 1/79;
(Continued)

(56) References Cited

U.S. PATENT DOCUMENTS 5,566,714 A * 10/1996 Miller ..................... F16L 29/04
137/614.04
8,028,718 B2 * 10/2011 Tiberghien .............. F16L 29/04
251/149.6

(Continued)

*Primary Examiner* — Minh Q Le
(74) *Attorney, Agent, or Firm* — Getech Law LLC; Jun Ye

(57) ABSTRACT

A manifold for a medical waste collection apparatus includes a fluid path connection portion and a storage connection portion. The storage connection portion includes a mounting connector in communication with the fluid path connection portion and coupled with the mounting base of the waste collection apparatus, and a docking valve arranged inside a connector cavity defined by inner walls of the connector. The docking valve is in an open state when the mounting connector is coupled with the mounting base, and a passage is formed between the storage connection portion and a waste collection container in the waste collection apparatus. The docking valve is in a closed state to close the connector cavity when the mounting connector is decoupled. The connection port between the manifold and the apparatus (Continued)

does not require manual opening or closing, thereby preventing waste from contaminating the environment, equipment and personnel, and enhancing convenience of use.

12 Claims, 14 Drawing Sheets

(51) Int. Cl.
    *F16L 29/02*       (2006.01)
    *A61B 50/36*       (2016.01)
    *F16L 39/00*       (2006.01)
    *F16L 41/03*       (2006.01)

(52) U.S. Cl.
    CPC ............... *A61M 1/78* (2021.05); *A61M 1/784* (2021.05); *A61M 1/79* (2021.05); *A61M 2205/125* (2013.01); *A61M 2205/75* (2013.01); *A61M 2205/7545* (2013.01); *F16L 39/00* (2013.01); *F16L 41/03* (2013.01)

(58) Field of Classification Search
    CPC .... A61M 2205/125; A61M 2205/7545; B01D 35/027; F16L 29/02; F16L 41/03; F16L 39/00; A61B 50/36
    USPC .......... 137/544, 68.14, 68.11, 513, 522, 523, 137/637.2
    See application file for complete search history.

(56) References Cited

U.S. PATENT DOCUMENTS

| | | | | |
|---|---|---|---|---|
| 9,194,634 | B2* | 11/2015 | Tiberghien | F16L 37/34 |
| 9,872,944 | B1* | 1/2018 | Willard | A61B 10/0045 |
| 10,288,198 | B2* | 5/2019 | Tiberghien | H05K 7/20272 |
| 10,948,117 | B2* | 3/2021 | Hummel | F16L 37/56 |
| 11,746,942 | B2* | 9/2023 | Durieux | F16L 29/04 |
| | | | | 251/149.6 |
| 2005/0139532 | A1* | 6/2005 | Hershberger | B01D 35/153 |
| | | | | 210/136 |
| 2007/0135778 | A1* | 6/2007 | Murray | A61B 50/10 |
| | | | | 604/317 |
| 2013/0312846 | A1* | 11/2013 | Eriksen | H05K 7/20772 |
| | | | | 137/315.01 |
| 2013/0341330 | A1* | 12/2013 | Michaels | A61M 1/604 |
| | | | | 220/495.06 |
| 2014/0130919 | A1* | 5/2014 | Hsieh | F16L 37/32 |
| | | | | 137/798 |
| 2016/0138746 | A1* | 5/2016 | Trent | F16L 37/12 |
| | | | | 251/148 |
| 2022/0133424 | A1* | 5/2022 | Liang | F16L 27/0804 |
| | | | | 141/231 |
| 2022/0412496 | A1* | 12/2022 | Nick | H05K 7/20272 |

* cited by examiner

MANIFOLD

CLAIM OF PRIORITY

This application is a 371 international application of PCT/CN2020/078376, filed on Mar. 9, 2020, which claims the benefit of priority from Chinese Patent Application with Application No. 201910039560.0, filed on Jan. 16, 2019 at China Intellectual Property Administration, entitled "WASTE COLLECTION DEVICE AND WASTE COLLECTION AND DISPOSAL SYSTEM" which is incorporated by reference herein in its entirety.

TECHNICAL FIELD

The invention relates generally to the field of medical apparatuses, and more particularly to a manifold, which is applied to a medical waste collection apparatus.

BACKGROUND

Waste in a liquid, semi-solid, and solid form and the like is inevitably generated in the course of performing a specific surgery. Specially, such waste includes human fluids, such as blood, and the perfusion solution introduced into a site in the body during a surgery. In addition, solid and semi-solid waste generated during a surgery includes tissue fragments and small pieces of surgical material that may be remained at the body site. In an ideal condition, the waste will be collected once it is generated, so that it will neither contaminate the surgical site nor become biohazard substances in the operating room or other location where a surgical procedure is performed.

There exist many types of waste collection systems for medical staffs to collect medical waste generated in a surgical procedure during or after the surgical procedure. The main principle thereof is that the waste generated at a surgical site is sucked into a specific collection container through a suction force generated by a vacuum source. That is, after the system is actuated, a suction force generated by a vacuum source reaches the surgical site, so that the waste is sucked into a specific collection container through a tube line contacted with the surgical site.

For instance, the existing NEPTUNE medical waste collection apparatus produced by Stryker is shown in FIG. 1. FIG. 1 is a schematic view of the structure of the aforementioned medical waste collection apparatus in prior art. The medical waste collection apparatus 1 includes a movable unit 11, a vacuum source 12, a manifold 14, and a waste collection container 13. In this technical solution, As a tube 15 for contacting with a surgical site is connected to the waste collection container 13 through the detachable manifold 14, the movable unit 11 can make the location of the medical waste collection apparatus 1 more flexible in use. However, by using the manifold 14, it is unnecessary to disinfect this apparatus, but only the waste collection container 13 needs to be cleaned and disinfected, thereby minimizing the risk of waste pollution.

Referring to FIG. 2, in the prior art solution, the port for the manifold 14 and the connection end of the medical waste collection apparatus 1 is sealed by a cover. The cover is opened while in use, and the cover of the manifold needs to be closed after the manifold is taken out. However, since the taking out and closing process requires manual operation, the manifold will inevitably move a certain distance during the process. In other prior art solutions, the port for the manifold 14 and the connection end of the medical waste collection apparatus 1 is provided with a barrier film that can be pierced or opened to achieve direct installation without opening a cover. However, the barrier film needs to be cut to be easily opened. Such film is easily broken and contaminated if a cover is not added, and it will still remain a certain extent of slot and not be able to be sealed after the manifold is taken out. In particular, the operation of taking out will also bring a certain vibration, the waste in the manifold, especially waste odors, may be leaked out during this process, causing pollution to personnel, equipment and the environment.

Moreover, if a similar port of the medical waste collection apparatus 1 for connecting to the manifold 14 cannot be closed in time, the waste, especially waste odors, may also be leaked out, causing pollution to personnel, equipment and the environment.

SUMMARY OF THE INVENTION

Various embodiments of the present invention are directed to provide a manifold. The port of the manifold for connecting with a medical waste collection apparatus does not need to be manually opened or closed, thereby avoiding waste pollution to the environment, equipment and personnel, and enhancing convenience of use.

As described above, an embodiment according to the present disclosure provides a manifold applied to a medical waste collection apparatus, comprising a fluid path connection portion and a storage connection portion. The storage connection portion includes a mounting connector configured to be in communication with the fluid path connection portion and coupled with the mounting base of the medical waste collection apparatus. The mounting connector includes a connector cavity defined by inner walls of the mounting connector.

The storage connection portion also includes a manifold end docking valve arranged inside the connector cavity, wherein the manifold end docking valve is in an open state when the mounting connector is coupled with the mounting base, and a passage is thus formed between the storage connection portion and a waste collection container disposed in the medical waste collection apparatus. The manifold end docking valve is in a closed state to close the connector cavity when the mounting connector is detached from the mounting base.

Further, the manifold end docking valve includes a sealing piston and a first elastic member, and the connector cavity includes a first cavity and a second cavity.

The sealing piston is movable between a first position and a second position. When the mounting connector is connected to the mounting base, the sealing piston is in the first position so that the sealing piston enters the second cavity, and a passage is formed between the storage connection portion and the waste collection container in the medical waste collection apparatus. When the mounting connector is detached from the mounting base, the sealing piston is in the second position so that the sealing piston returns to the first cavity and seals the connector cavity.

The first elastic member cooperates with the sealing piston to make the sealing piston rebound from the first position to the second position.

Further, the sealing piston includes a piston base and a piston rod disposed on the piston base.

Further, a connector sealing ring is disposed between the piston base and the connector cavity, so that when the sealing piston is in the second position, the connector sealing ring is mated with the sealing piston to seal the connector cavity.

Further, the connector sealing ring is positioned in an inner sealing groove, and the inner sealing groove is disposed on the piston base or in an inner wall of the connector cavity.

Further, the inner diameter of the second cavity is greater than the inner diameter of the first cavity.

Further, a guide tube for accommodating the movement of the piston rod is disposed in the mounting connector.

Further, the first elastic member is a spring.

Further, the spring is sleeved on the guide tube and the piston rod.

Further, a filtering bin is disposed between the fluid path connection portion and the storage connection portion.

Further, a filter screen is positioned in the filtering bin.

Further, the guide tube is disposed on the filter screen.

Further, the mounting connector further includes a sleeve head sleeved on the first cavity.

Further, a connector sealing ring is provided in the sleeve head.

Further, the sleeve head is also provided with a mounting sleeve groove that can be coupled with the outer wall of the first cavity.

Further, the connector cavity further includes a third cavity, which has an inner diameter greater than the inner diameter of the second cavity.

Further, the manifold also includes a vacuum connection portion for connecting to the vacuum source in an airflow path manner, and meanwhile the vacuum connection portion is also connected to the waste collection container in an airflow path manner so that a suction force can be provided for the waste collection container.

The beneficial effects of implementing various embodiments of the present disclosure can be provided as follows: First, the manifold in the embodiments may not need to be provided with an additional sealing cover, so that it is unnecessary to manually open the sealing cover and then mounting it to the medical waste collection apparatus in use, while a passageway is automatically formed during installation. At the same time, the ports for connecting the manifold and the medical waste collection apparatus can be automatically sealed after the manifold is taken out, thereby avoiding waste pollution to the environment, equipment and personnel. Secondly, the manifold according to the embodiments can be directly inserted into the medical waste collection apparatus during installation without manually opening the sealing cover in advance, and manually sealing the port of the manifold for connecting with the medical waste collection apparatus after use, making the operation easier and providing improved usage convenience.

DESCRIPTION OF THE DRAWINGS

To describe the technical solutions of the embodiments of the present disclosure more clearly, the following briefly introduces the accompanying drawings required for describing the embodiments of the present disclosure or the prior art. Apparently, the accompanying drawings described below illustrate merely some embodiments of the present disclosure, and one of ordinary skill in the art may derive other drawings from the accompanying drawings without creative efforts.

DETAILED DESCRIPTION

The description of the following embodiments is to illustrate specific implementable embodiments in the present disclosure with reference to accompanying drawings. The directional terms mentioned in the present disclosure, such as "upper", "downward", "front", "rear", "left", "right", "inner", "outer", "side", etc., are only directions by referring to the accompanying drawings. Therefore, the directional terms herein are used to illustrate and understand the present invention, and are not intended to limit the scope of the present invention.

In order to make the objectives, technical solutions and advantages of the present disclosure clearly and fully understandable, the present disclosure will be further described in detail below in conjunction with the accompanying drawings.

Figure 3:
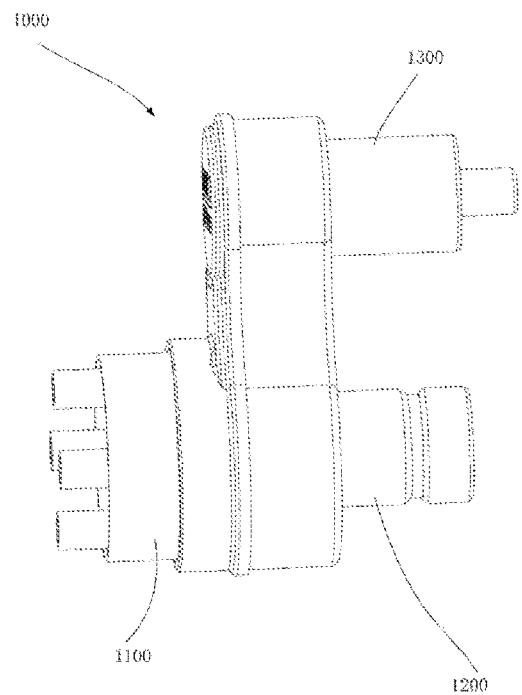
FIG. 3 is a schematic structural view illustrating a first embodiment of a manifold according to the present disclosure.
Figure 4:
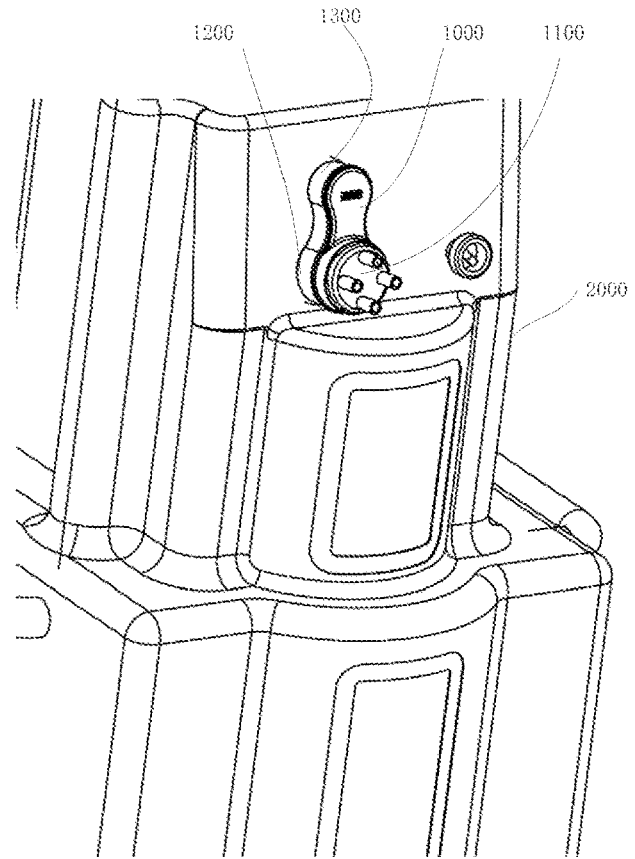
FIG. 4 is a view illustrating the connecting structure of a manifold and a medical waste collection apparatus according to the present disclosure.

FIG. 3 shows a manifold 1000 according to an embodiment of the present disclosure. As shown in FIGS. 3-4, the manifold 1000 is utilized in a medical waste collection apparatus 2000 shown in FIG. 4. In the embodiment, the manifold 1000 includes a fluid path connection portion 1100, a storage connection portion 1200, and a vacuum connection portion 1300.

Figure 6:
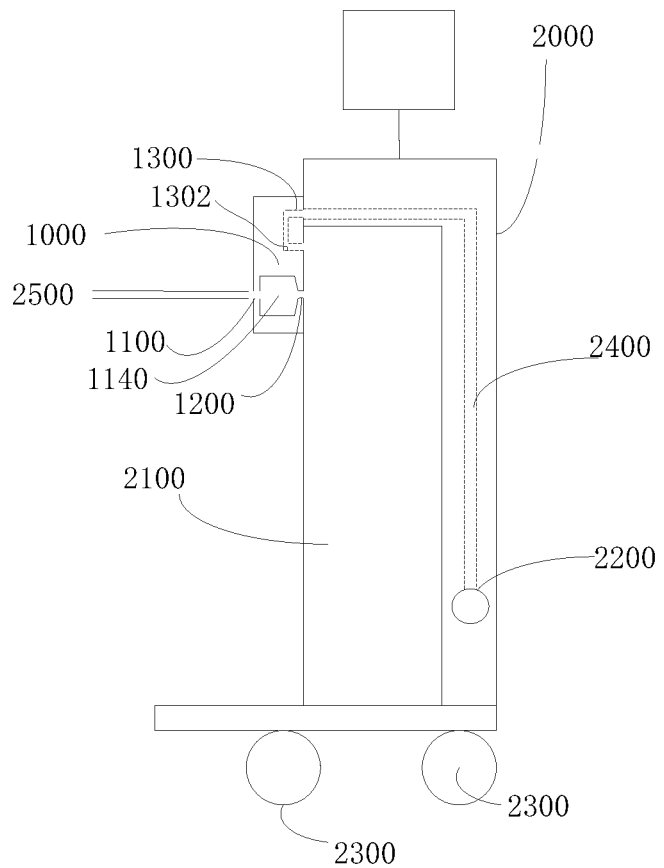
FIG. 6 is a schematic view illustrating the pipeline connection of a manifold and a medical waste collection apparatus according to one embodiment of the present disclosure.

In this embodiment, the fluid path connection portion 1100 for introduction of medical waste is as particularly shown in FIG. 6. FIG. 6 is a schematic view of a connection between the manifold 1000 and the medical waste collection apparatus 2000 according to the present disclosure. The fluid path connection portion 1100 is connected to an external suction tube line 2500, which may be connected with a suction connector (not shown). The suction connector may be a separate connector or be attached to a surgical device. The suction force at the suction connector can facilitate waste to be delivered to the fluid path connection portion 1100 through the external suction tube line 2500.

The storage connection portion 1200 has an end in fluid communication with the fluid path connection portion 1100. The storage connection portion 1200 is used to attach with a waste collection container 2100 of the medical waste collection apparatus 2000, so that medical waste can be entered into the waste collection container 2100 of the medical waste collection apparatus 2000.

Figure 1:
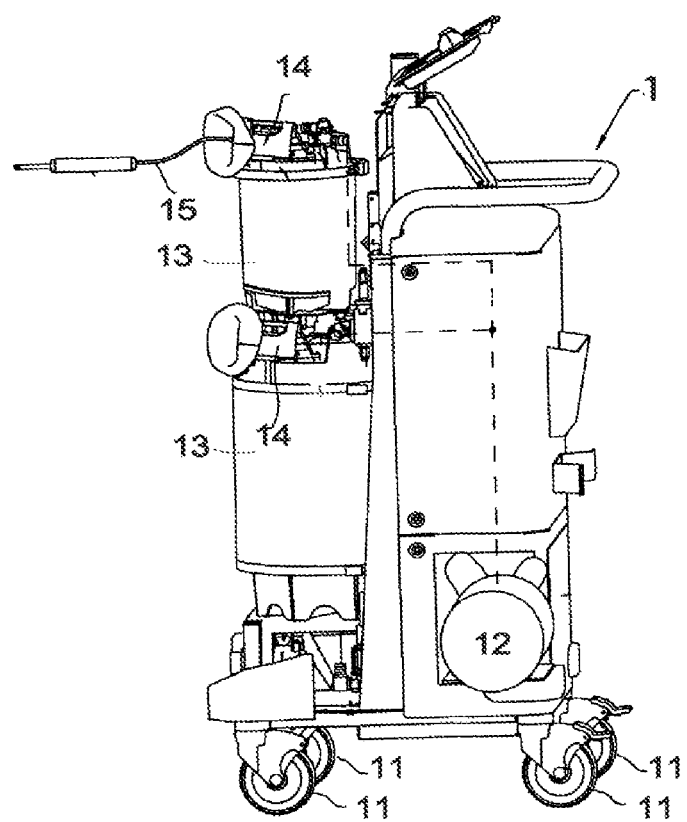
FIG. 1 is a schematic view of the structure a medical waste system with using an existing manifold.
Figure 2:
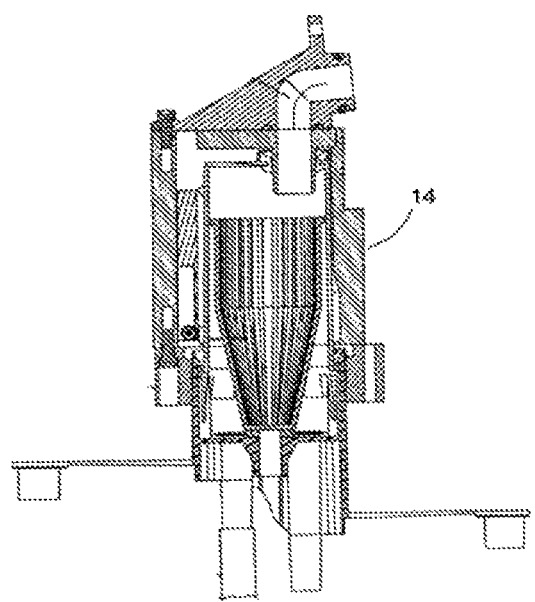
FIG. 2 is a schematic view of the structure of an existing manifold.
Figure 5:
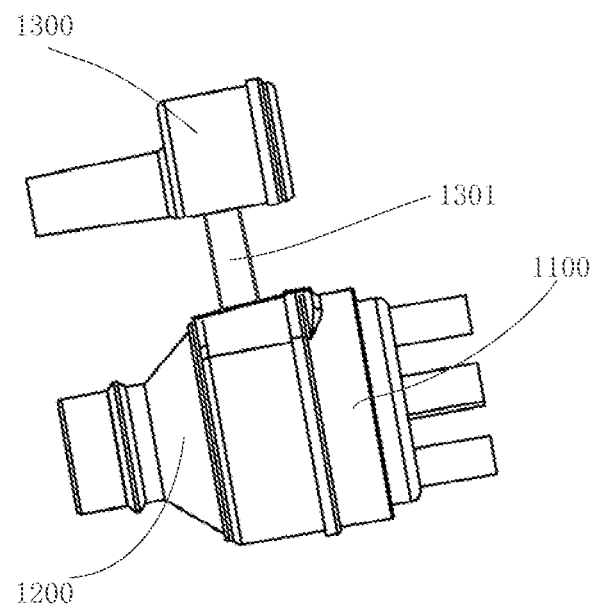
FIG. 5 is a schematic structural view illustrating a second embodiment of a manifold according to the present disclosure.

In addition, the manifold 1000 further includes a vacuum connection portion 1300 for connecting to a vacuum source, as shown in FIG. 6. FIG. 6 depicts a medical waste collection apparatus 2000 including a vacuum source 2200. In other embodiments, the vacuum source 2200 may not be accommodated in the medical waste collection apparatus 2000, but is used as a separate device. Meanwhile, the vacuum connection portion 1300 is connected to the waste collection container 2100 in an airflow path manner to provide a suction force for the waste collection container 2100. As shown in FIG. 2, the vacuum connection portion 1300, the fluid path connection portion 1100, and the storage connection portion 1200 forms an integrated structure, and the vacuum connection portion 1300, the fluid path connection portion 1100, and the storage connection portion 1200 are all housed in a same housing. However, the aforementioned structure is merely an embodiment of the present disclosure. In other embodiments, for example, the embodiment of a manifold shown in FIG. 5, the vacuum connection portion 1300 can be connected to the fluid path connection portion 1100 and the storage connection portion 1200 through a connecting tube 1301. The connecting tube 1301 may be a hose or a rigid tube, and the connecting tube may be configured to have at least one end for connection in a detachable way.

In the embodiment shown in FIG. 6, the manifold 1000 is attached to, preferably, is plugged into the medical waste collection apparatus 2000. The medical waste collection apparatus 2000 includes a waste collection container 2100, a vacuum source 2200 and a movable unit 2300. The vacuum connection portion 1300 is connected to the vacuum source 2200 through an inner vacuum tube line 2400 of the medical waste collection apparatus 2000, and meanwhile a suction connection path 1302 is formed inside the vacuum connection portion 1300, and the suction connection path 1302 is connected to the waste collection container 2100, so that the vacuum source 2200 can suck the waste collection container 2100 to form a suction force in the waste collection container 2100. The fluid path connection portion 1100 is connected to the storage connection portion 1200, and the storage connection portion 1200 is connected to the waste collection container 2100. In the embodiment as shown in FIG. 6, a path for performing suction on the waste collection container 2100 is disposed in the vacuum connection portion 1300. That is, the connection path 1302 for gas suction is separately isolated from the path for transmitting waste to the waste collection container 2100.

Figure 7:
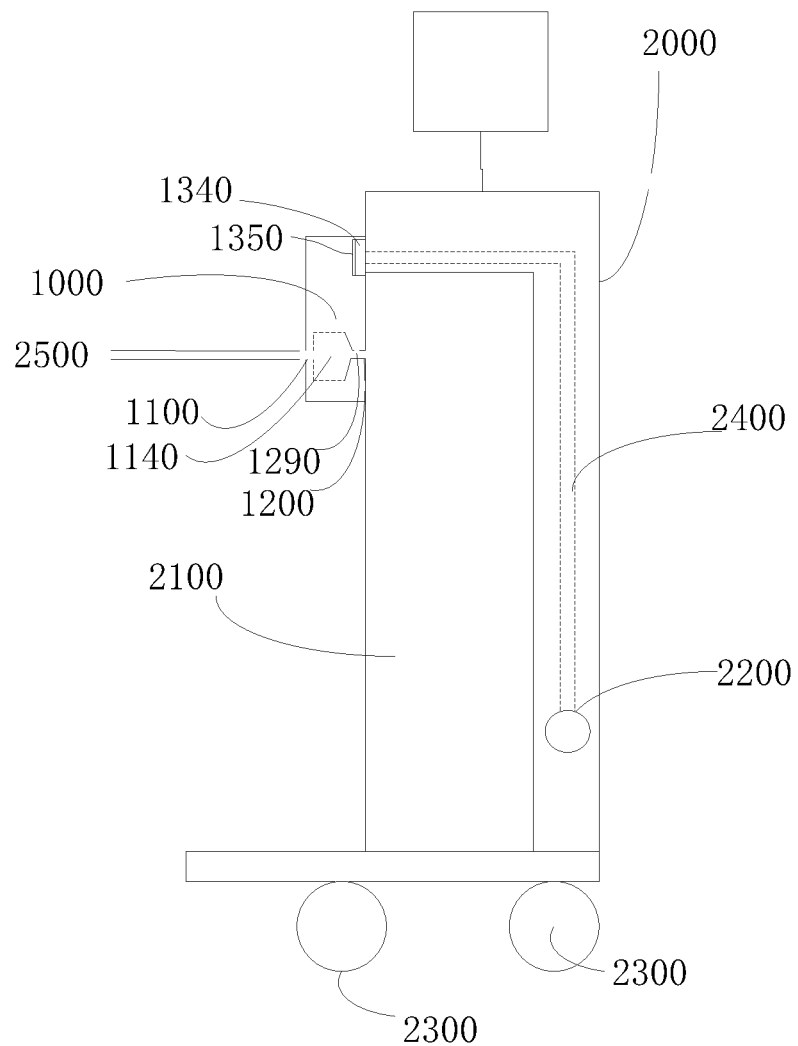
FIG. 7 is a schematic view illustrating the pipeline connection of a manifold and a medical waste collection apparatus according to another embodiment of the present disclosure.

In the embodiment shown in FIG. 7, the vacuum connection portion 1300 is connected to the vacuum source 2200 through the vacuum tube line 2400 inside the medical waste collection apparatus 2000, and the vacuum connection portion 1300 is connected with at least the storage connection portion 1200 in an airflow path manner. The vacuum source 2200 can perform a suction procedure on the waste collection container 2100 through the path between the storage connection portion 1200 and the waste collection container 2100 to form a suction force therein. That is, there is a combined tube line 1201 provided between the storage connection portion 1200 and the waste collection container 2100, for delivering medical waste into the waste collection container 2100, and also forming a connection from the vacuum source 2200 to the vacuum connection portion 1300 and a connection from vacuum connection portion 1300 to the waste collection container 2100 in an airflow path manner, so that the vacuum source 2200 may perform suction on the waste collection container 2100.

Figure 8:
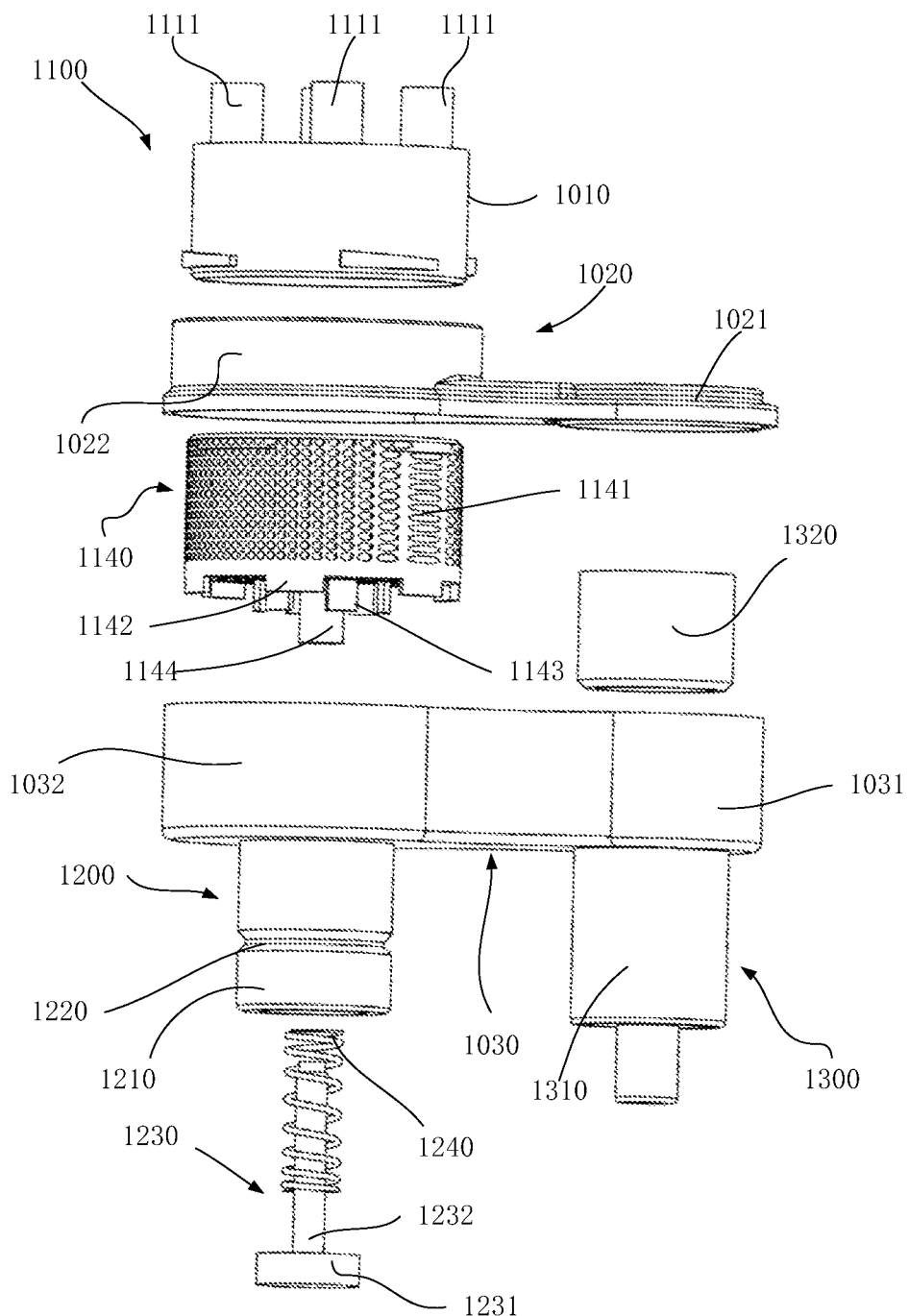
FIG. 8 is a schematic view illustrating the portions of the manifold shown in FIG. 3 of the present disclosure.

Referring to FIG. 8, FIG. 8 illustrates a schematic view of the portions of the manifold shown in FIG. 3 of the present disclosure. The manifold as shown in FIG. 8 (including a manifold 1000) includes a fluid path connection portion 1100, a storage connection portion 1200 and a vacuum connection portion 1300. The fluid path connection portion 1100 and the vacuum connection portion 1300 share a common first housing 1020, and the storage connection portion 1200 and the vacuum connection portion 1300 share a common second housing 1030. The first housing 1020 and the second housing 1030 are hermetically connected. However, those skilled in the art may also fabricate an integrated structure of the first housing 1020 and the second housing 1030 depending on requirements of actual use and processing.

The fluid path connection portion 1100 includes a connection base 1010, a first lower end housing part 1022 of the first housing 1020, and a second lower end housing part 1032 of the second housing 1030. The fluid path connection portion 1100 also includes at least one introduction connector 1111 capable of being connected to an external suction tube line, and the introduction connector 1111 extends from the outer surface 1110 of the connection base 1010 and is configured to be a structure that may be assembled with the external suction tube line 2500. In a preferred embodiment, the number of introduction connectors 1111 is four.

Figure 9:
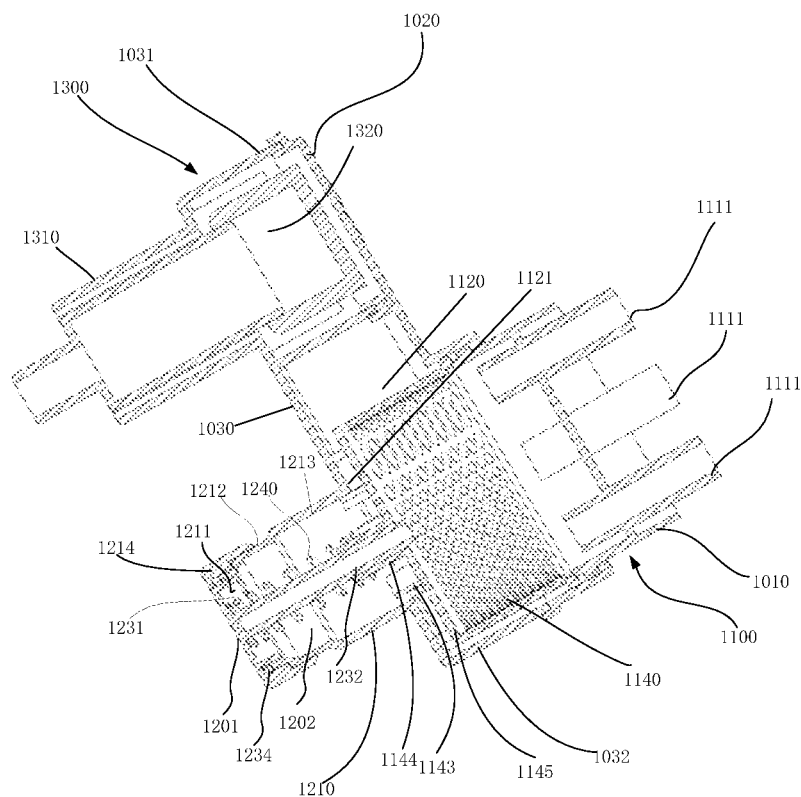
FIG. 9 is a cross-sectional view of the manifold shown in FIG. 3 of the present disclosure.

As shown in FIG. 9, FIG. 9 is a cross-sectional view of the manifold shown in FIG. 3 of the present disclosure. The fluid path connection portion 1100 also includes at least one liquid filtering bin 1120, and the medical waste is introduced through the introduction connector 1111 and then into the liquid filtering bin 1120 for filtration therein. The introduction connector 1111 is connected to the external suction tube line 2500, which may be connected to a suction connector (not shown). The suction connector may be a separate connector or be attached to a surgical device. The suction force at the suction connector transports the waste through the external suction tube 2500, passing the introduction connector 1110 and into the liquid filtering bin 1120 of the fluid path connection portion 1100 for filtration. The liquid filtering bin 1120 may filter and store medical waste in the manifold 1000, which may block the medical waste collection apparatus 2000 and any subsequent device for transporting waste liquid, and it will be discarded together with the manifold after completion of the waste collection procedure. In a conventional liquid filtering bin 1120, a filter screen or other structure may be provided at the port connected to the storage connection portion 1200 for implementing filtration. In the embodiment shown in FIG. 9, the liquid filtering bin 1120 also includes an independent filter screen 1140 configured to be embedded in the liquid filtering bin 1120 and have a shape roughly similar as an inner surface of the liquid filtering bin 1120.

As shown in FIGS. 8 and 9, in this embodiment, the liquid filtering bin 1120 is consisted of the inner surface of the connection base 1010, the inner surface of the first lower end housing part 1022 of the first housing 1020, and the inner surface of the second lower end housing portion 1032 of the second housing 1030. Among them, the connection base 1010 is fitted in the first lower end housing part 1022 of the first housing 1020.

Figure 11:
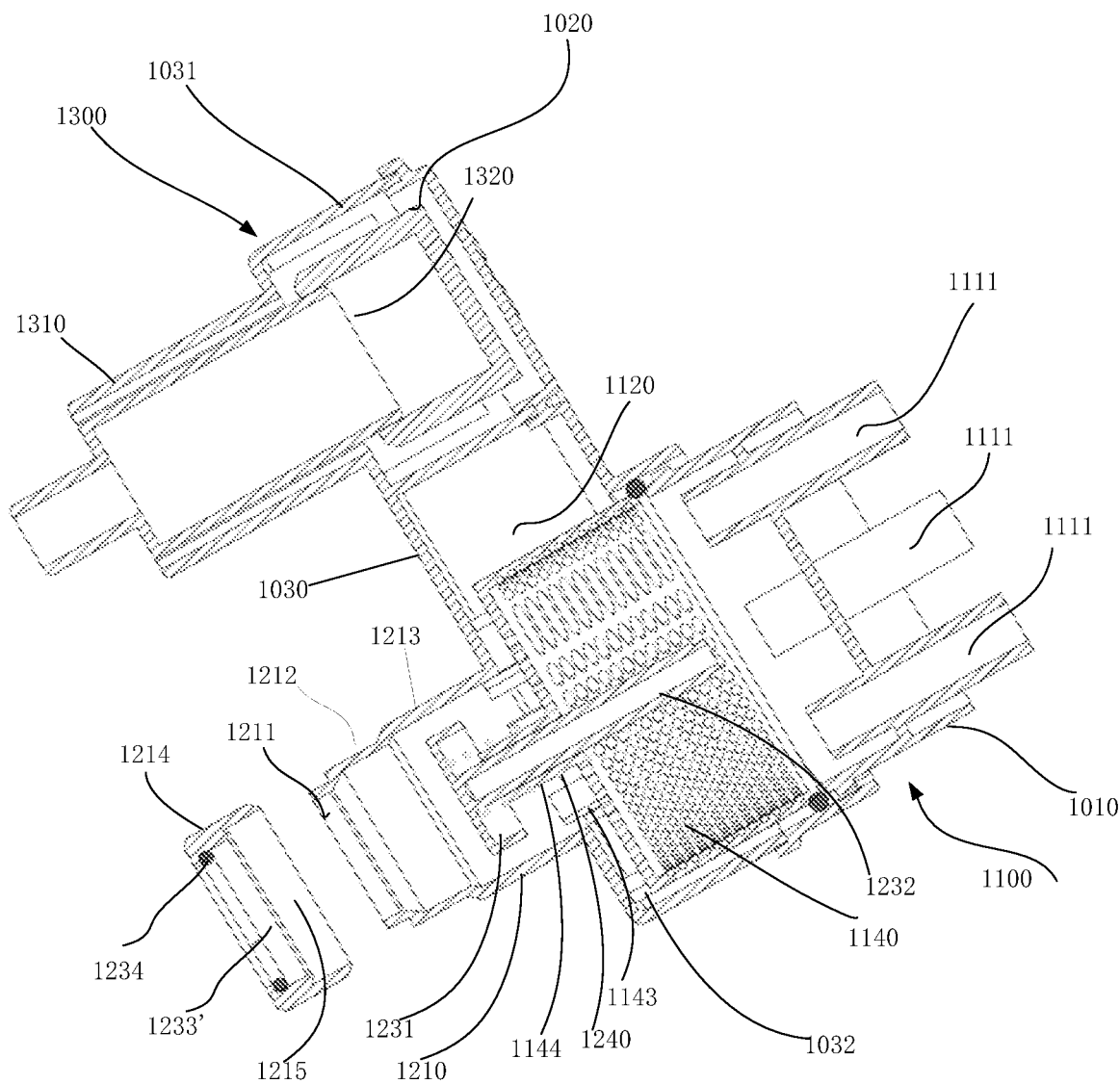
FIG. 11 is a schematic view illustrating parts of a second embodiment of a manifold according to the present disclosure.

The storage connection portion 1200 has one end in fluid communication with the fluid path connection portion 1100, which is used for being connected to the waste collection container 2100 of the medical waste collection apparatus 2000, so that medical waste can be delivered into the waste collection container 2100 of the medical waste collection apparatus 2000. The storage connection portion 1200 is positioned at the lower end of the second housing 1030 and is an outward extension of the lower end of the second housing 1030. Referring to FIG. 8 and FIG. 11, the storage connection portion 1200 includes a mounting connector 1210 for coupling with the medical waste collection apparatus 2000, and meanwhile medical waste can also be transported to the waste collection container 2100 through the mounting connector 1210. As shown in FIG. 7, a combined tube line 1290 can be formed in the mounting connector 1210. The mounting connector 1210 is provided with a fixed locking groove 1220 for fixing the manifold 1000.

Referring to FIG. 8, the storage connection portion 1200 also includes a sealing piston 1230, which can be opened to form a passage between the storage connection portion 1200 and the waste collection container 2100 after the mounting connector 1210 is coupled with the medical waste collection apparatus 2000, while the sealing piston 1230 seals the storage connection portion 1200 once the mounting connector 1210 is decoupled from the medical waste collection apparatus 2000. Specifically, the sealing piston 1230 includes a piston base 1231 and a piston rod 1232. An elastic member 1240 is also disposed between the sealing piston 1230 and the inner surface of the mounting connector 1210. The elastic member 1240 may be deformed when the mounting connector 1210 is coupled with the medical waste collection apparatus 2000, and make the sealing piston 1230 reset by the elastic force of the deformation when the mounting connector 1210 is decoupled from the medical waste collection apparatus 2000.

As shown in FIGS. 8 and 9, the manifold 1000 also includes a vacuum connection portion 1300 for connecting to a vacuum source. Referring to FIG. 6, FIG. 6 illustrates a medical waste collection apparatus 2000 including a vacuum source 2200, however in other embodiments, the vacuum source 2200 may not be disposed in the medical waste collection apparatus 2000, while it can be used as an independent device. Meanwhile, the vacuum connection portion 1300 is connected to the waste collection container 2100 by way of an airflow path to provide a suction force to the waste collection container 2100.

Specifically, the vacuum connection portion 1300 includes a vacuum connection tube 1310, through which the vacuum connection portion 1300 is connected to the vacuum source 2200. The vacuum connection portion 1300 includes a first upper end housing portion 1021 of the first housing 1020 and a second upper end housing portion 1031 of the second housing 1030. The vacuum connection portion 1300 also includes a fixing element for detachably fixing the vacuum connection portion 1300 to the medical waste collection apparatus 2000. In the present embodiment, the vacuum connection tube 1310 is inserted into the corresponding interface of the medical waste collection apparatus 2000 for serving as a fixing element. That is, the fixing element is the vacuum connection tube 1310 in this embodiment. The vacuum connection tube 1310 has a first port 1311 and a second port 1312. The outer diameter of the first port 1311 is smaller than the outer diameter of the second port 1312, so that the axially cross-sectional profile of the vacuum connection tube 1310 is defined in a trapezoidal structure. Thus, a certain dislocation space can be left during coupling, and a sealing and fixing connection can be achieved when the coupling is finally completed. In other embodiments, the vacuum connection tube 1310 and the fixing element may be different components.

Further, referring to FIGS. 9 and 11, the vacuum connection portion 1300 also includes an empty chamber 1320 capable of forming a large volume of negative-pressure chamber outside a gas filtering assembly and a water blocking membrane. In comparison with direct connection of narrow pipelines, the negative-pressure chamber may temporarily store a small amount of liquid in the sucked waste without blocking the pipeline. The vacuum connection portion 1300 can realize the vacuum connection portion 1300 being in airflow communication with the storage connection portion 1200 through a narrow gap (not shown) formed between the first housing 1020 and the second housing 1030 and a partially open space, such that the vacuum source 2200 can suck the waste collection container 2100 and finally collect medical waste into the manifold 1000 and into the waste collection container 2100 through the fluid path connection portion 1100. In the embodiment of FIGS. 8-12, the connection of a gas path formed between the vacuum connection portion 1300 and the waste collection container 2100 does not pass through the storage connection portion 1200, but there is a special gas passage connected between the vacuum connection portion 1300 and the waste collection container 2100, as shown in FIG. 7.

Figure 12:
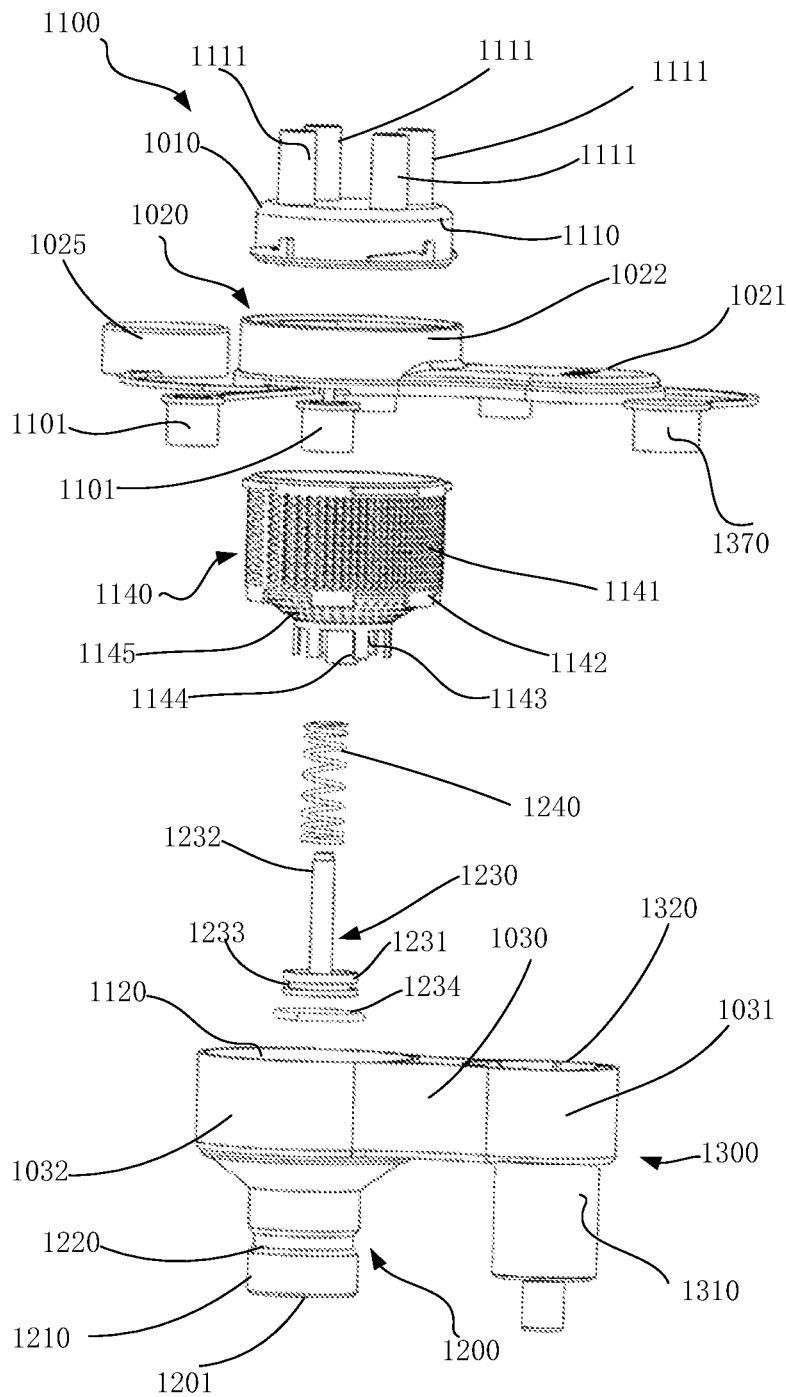
FIG. 12 is a schematic view illustrating a first side cross-sectional view of a third embodiment of a manifold according to the present disclosure.

Referring to FIG. 12, the fluid path connection portion 1100 further includes a first tube cap 1101 capable of being coupled with the introduction connector 1111, the number of which may be disposed with the same as the introduction connectors 1111. The vacuum connection portion 1300 also includes a second tube cap 1370 capable of being coupled with the vacuum connection tube 1310. The storage connection part 1200 further includes a third tube cap 1025 capable of being coupled with the mounting connector 1210.

Referring to FIGS. 4, 6 and 7, various embodiments according to the present disclosure also provide a medical waste collection apparatus, which includes a manifold 1000 described in the disclosure.

Referring to FIG. 4, FIG. 4 is a schematic view of mounting the manifold 1000 on the mounting base 3000 of the medical waste collection apparatus 2000. Among them, the mounting base 3000 is connected to the waste collection container 2100, and the waste of entering the manifold 1000 enters into the waste collection container 2100 through the tube connected between the mounting base 3000 and the waste collection container 2100.

As shown in FIGS. 8-18, the storage connection portion 1200 of the manifold 1000 shown in FIGS. 8 and 9 includes a mounting connector 1210 and a manifold end docking valve 1201. The manifold end docking valve 1201 is disposed in a connector cavity 1202 defined by interior walls of the mounting connector. The mounting connector 1210 is coupled with the mounting base 3000 of the medical waste collection apparatus 2000. The manifold end docking valve 1201 is in an open state when the mounting connector 1210 is inserted into the mounting base 3000, and a passage is formed between the storage connection portion 1200 and the waste collection container 2100 in the medical waste collection apparatus 2000. The manifold end docking valve 1201 is in a closed state to close the connector cavity 1202, when the mounting connector 1210 is detached from the mounting base 3000.

The manifold 1000 shown in FIG. 9, which is applied to a medical waste collection apparatus 2000, includes a fluid path connection portion 1100 and a storage connection portion 1200. The storage connection portion 1200 includes a mounting connector 1210 and a manifold end docking valve 1201. The mounting connector 1210 communicates with the fluid path connection portion 1100 and is used to couple with the mounting base 3000 of the medical waste collection apparatus 2000. The manifold end docking valve 1201 is disposed in the connector cavity 1202 formed by interior walls of the mounting connector 1210. The manifold end docking valve 1201 is in an open state when the mounting connector 1210 is connected to the mounting base 3000, and a passage is formed between the storage connection portion 1200 and the waste collection container 2100 in the medical waste collection apparatus 2000. The manifold end docking valve 1201 is in a closed state to close the connector cavity 1202 when the mounting connector 1210 is detached from the mounting base 3000.

The manifold end docking valve 1201 includes a sealing piston 1230 and a first elastic member 1240. The connector cavity 1202 includes a first cavity 1211 and a second cavity 1212. The sealing piston 1230 can be moved between a first position and a second position. Once the mounting connector 1210 is inserted into the mounting base 3000, the sealing piston 1230 is in the first position so that the sealing piston 1230 enters the second cavity 1212, and a passage is formed between the storage connection portion 1200 and the waste collection container 2100 in the medical waste collection apparatus 2000. While the mounting connector 1210 is detached from the mounting base 3000, the sealing piston 1230 is in the second position so that the sealing piston 1230 returns back to the first cavity 1211 and closes the connector cavity 1202.

Specifically, the inner diameter of the second cavity 1212 is greater than the inner diameter of the first cavity 1211. When the mounting connector 1210 is inserted into the mounting base 3000, the sealing piston 1230 is pushed to the first position by an ejector rod 3130 disposed in the mounting base 3000. At this time, the sealing piston 1230 enters into the second cavity 1212. Since the inner diameter of the second cavity 1212 is greater than the inner diameter of the first cavity 1211, a gap existing between the sealing piston 1230 and the second cavity 1212 constitutes an aisle therein, and thus a passage is formed therein between the storage connection portion 1200 and the waste collection container 2100 in the medical waste collection apparatus 2000.

When the mounting connector 1210 is detached from the mounting base 3000, the first elastic member 1240 cooperates with the sealing piston 1230 to make the sealing piston 1230 rebound from the first position to the second position. The sealing piston 1230 is located in the first cavity 1211 when it is in the second position. At this time, the sealing piston 1230 and the first cavity 1211 form a sealed connection to seal the connector cavity 1202.

As shown in FIG. 11, the connector cavity 1202 further includes a third cavity 1213 having an inner diameter that is greater than the inner diameter of the second cavity 1212. When the mounting connector 1210 is inserted into the mounting base 3000, the sealing piston 1230 is pushed to the first position by the ejector rod 3130 of the mounting base 3000. At this time, the sealing piston 1230 enters the second cavity 1212 or the third cavity 1213. Since the inner diameters of both the second cavity 1212 and the third cavity 1213 are greater than the inner diameter of the first cavity 1211, a gap existing between the sealing piston 1230 and the second cavity 1212 constitutes an aisle therein and thus a passage is formed therein between the storage connection portion 1200 and the waste collection container 2100 in the medical waste collection apparatus 2000. Preferably, the sealing piston 1230 can be moved between the second cavity 1212 and the third cavity 1213 by adjusting the ejector rod 3130 so as to adjust the liquid flux in the connector cavity 1202.

Figure 10:
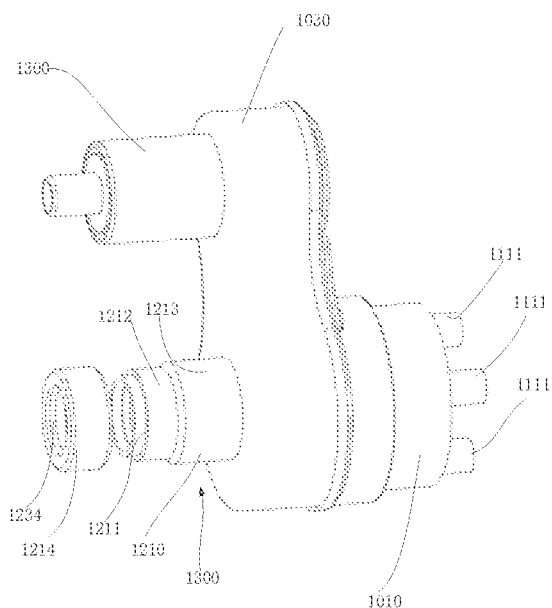
FIG. 10 is a schematic view illustrating the structure of a second embodiment of a manifold according to the present disclosure.
Figure 13:
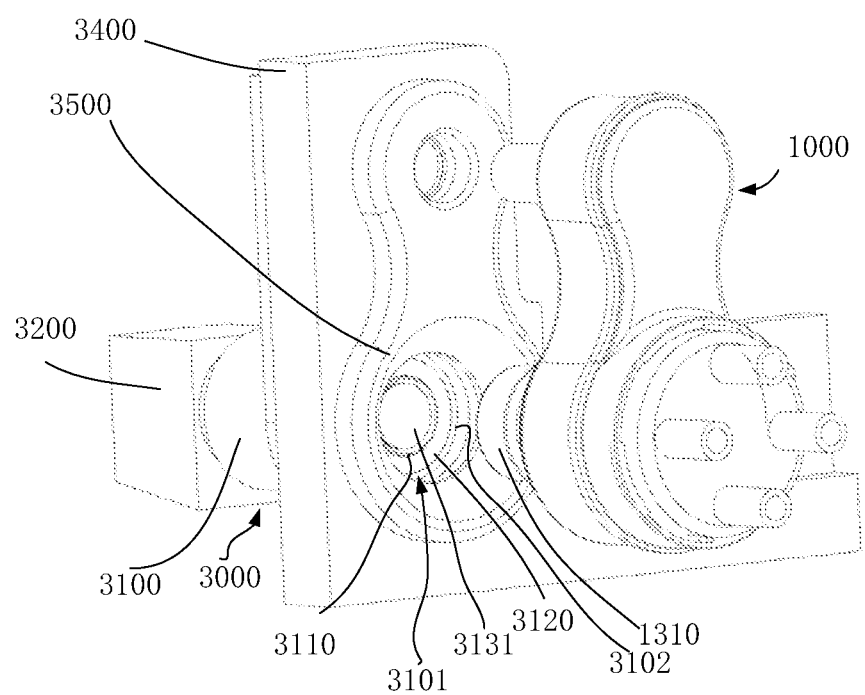
FIG. 13 is a structural view illustrating a manifold and a mounting base being in a detached state according to the present disclosure.

Referring to FIGS. 8-11, the sealing piston 1230 includes a piston base 1231 and a piston rod 1232 disposed on the piston base 1231. In order to achieve a better sealing effect, a connector sealing ring 1234 is arranged between the piston base 1231 and the connector cavity 1202 so that the connector sealing ring 1234 is mated with the sealing piston 1230 to seal the connector cavity 1202 when the sealing piston 1230 is in the second position. The connector sealing ring 1234 is positioned in an inner sealing groove 1233, as shown in FIG. 13, which is a schematic view of the portions of a fifth embodiment of a manifold according to the present disclosure. The inner sealing groove 1233 can be formed on the piston base 1231. Or, as shown in FIGS. 10 and 11, FIG. 10 is a schematic structural view illustrating a fourth embodiment of a manifold according to the present disclosure, and FIG. 11 is a cross-sectional view of the fourth embodiment of the manifold according to the present disclosure. The mounting connector 1210 is also provided with a sleeve head 1214, in which an inner sealing groove 1233 can be disposed. Specifically, the sleeve head 1214 includes an inner sealing groove 1233' and a mounting sleeve groove 1215. The inner sealing groove 1233' has an inner diameter equal to the inner diameter of the first cavity 1211, and the mounting sleeve groove 1215 is hermetically mated with the first cavity 1211, and the sleeve head 1214 can be mounted on the first cavity 1211 by ultrasonic welding or cementing.

As shown in FIG. 9, the filtering bin 1120 disposed between the fluid path connection portion 1100 and the storage connection portion 1200 is provided with a filter screen 1140, which is a cylindrical structure. The filter screen 1140 includes an opening in the upper portion, many filtering holes 1141 disposed on the side wall, and a number of first supporting sheets 1142 disposed thereon to be in contact with the bottom part 1121 of the filtering bin 1120, so that a gap is formed between the bottom mesh surface 1145 of the filter screen 1140 and the bottom part 1121 of the filtering bin 1120 so as to protect the filter screen 1140 from blocking. The number of the first supporting sheets 1142 is preferably 4-8. At the same time, the filter screen 1140 is also provided with a number of second supporting sheets 1143 to be inserted into the connector cavity 1202 to fix the filter screen 1140. The number of second supporting sheets 1143 is preferably 4-6. The filter screen 1140 is also provided with a guide tube 1144 that can accommodate the movement of the piston rod 1232, and the guide tube 1144 is arranged on the bottom mesh surface 1145. The guide tube 1144 has a length on which the first elastic member 1240 may be sleeved, and the first elastic member 1240 may be a spring, which has one end sleeved on the guide tube 1144, and the other end sleeved on the piston rod 1232.

In the embodiment shown in FIG. 12, the filter screen 1140 has an upper cylindrical structure, and the bottom mesh screen 1145 has an approximately conical structure.

When the mounting connector 1210 is inserted into the mounting base 3000, the sealing piston 1230 is pushed to the first position by the ejector rod 3130 in the mounting base 3000. At this time, the piston rod 1232 enters the filter screen 1140 through the guide tube 1144, and the piston base 1231 compresses the spring 1240. When the mounting connector 1210 is detached from the mounting base 3000, the spring 1240 elastically deforms to push the piston base 1231 to make the sealing piston 1230 rebound from the first position to the second position.

The following beneficial effects by implementing the embodiments of the present disclosure can be provided: First, in the embodiments of the present invention, a vacuum connection portion is added in a manifold so that a vacuum source does not need to be directly connected to a waste collection container, thereby avoiding any complex connection structure being arranged between the waste collection container and the vacuum source, and providing easy detachment and maintenance for both the vacuum source and the waste collection container. Secondly, the waste collection container and the vacuum source can be effectively separated by the manifold after the manifold is placed, thereby reducing the risk of waste pollution to devices. Moreover, the manifold is a disposable component so that the waste in the waste collection container is hard to directly contact the vacuum source regardless of whether the manifold is in use or not, thereby effectively reducing the risk of waste contaminating the device. Next, the manifold can be designed without an additional sealing cover, and thus a sealing cover does not need to be manually opened to mount the manifold to the medical waste collection apparatus in use, while a passageway is automatically formed at the time of the mounting. And meanwhile the manifold can automatically seal its port for connecting with the medical waste collection apparatus after the manifold is taken out, and the medical waste collection apparatus can also automatically seal its port for connection with the manifold, thereby avoiding waste pollution to the environment, equipment and personnel. In addition, the manifold according to an embodiment can be directly inserted into the medical waste collection apparatus during installation without manually opening a sealing cover in advance, and there is also no need to manually seal the port for connecting the manifold and the medical waste collection apparatus after use, thereby making operations easier and providing improved convenience of use.

Referring to FIG. 13, it is a view for illustrating the parts of the mounting base 3000 of the medical waste collection apparatus 2000. As shown in FIGS. 6-7, the medical waste collection apparatus 2000 includes a waste collection container 2100 for collecting waste and a mounting base 3000 for communicating the manifold 1000 with the waste collection container 2100 after the manifold 1000 is mounted. The mounting base 3000 includes a base housing 3100, a base end docking valve 3101 disposed in the base housing 3100 and a collection container connection portion 3200. A mounting inlet 3102 for coupling with the mounting connector 1210 and an internal cavity 3103 for guiding waste are formed in the base housing 3100. The base end docking valve 3101 is disposed in the base housing 3100. When the mounting connector 1210 is inserted, the base end docking valve 3101 is opened and a fluid passage is formed between the manifold 1000 and the waste collection container 2100. When the mounting connector 1210 is detached from the mounting base 3000, the base end docking valve 3101 closes the mounting inlet 3102. The collection container connection portion 3200 communicates with the internal cavity 3103 of the base and can be in fluid communication with the waste collection container 2100.

Figure 14:
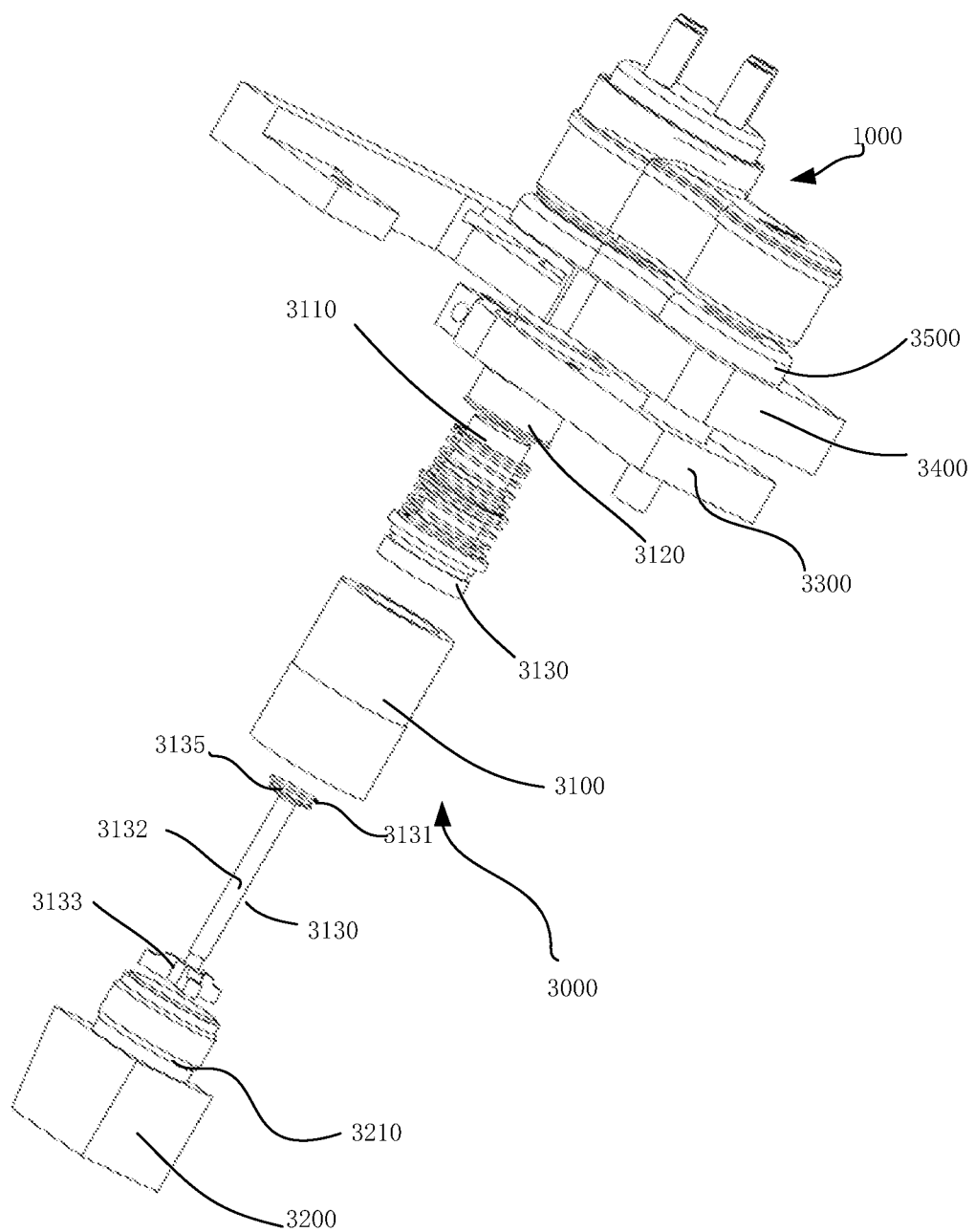
FIG. 14 is a view illustrating the parts of an embodiment of a mounting base according to the present disclosure.

Referring to FIG. 14, the base end docking valve 3101 includes an ejector rod 3130 and a floating sleeve 3110. The ejector rod 3130 is fixed in the base housing 3100 and the floating sleeve 3110 is sleeved outside the ejector rod 3130 and is positioned in the base housing 3100. The floating sleeve 3110 can move in an axial direction with using the ejector rod 3130 as an axis. When the mounting connector 1210 is inserted into the mounting inlet 3102, the ejector rod 3130 pushes the sealing piston 1230 of the manifold end docking valve 1201 of the manifold 1000 to the first position. At this time, the floating sleeve 3110 moves to a third position for a sealed connection with the mounting connector 1210. In the embodiment at this time, the mounting connector 1210 directly pushes the floating sleeve 3110 to move downward and separate from the ejector rod 3130, so that the base end docking valve 3101 is opened. When the mounting connector 1210 is separated from the mounting base 3000, the floating sleeve 3110 returns to a fourth position at which the floating sleeve 3110 is engaged with the ejector rod 3130 to close the base end docking valve 3101.

Figure 15:
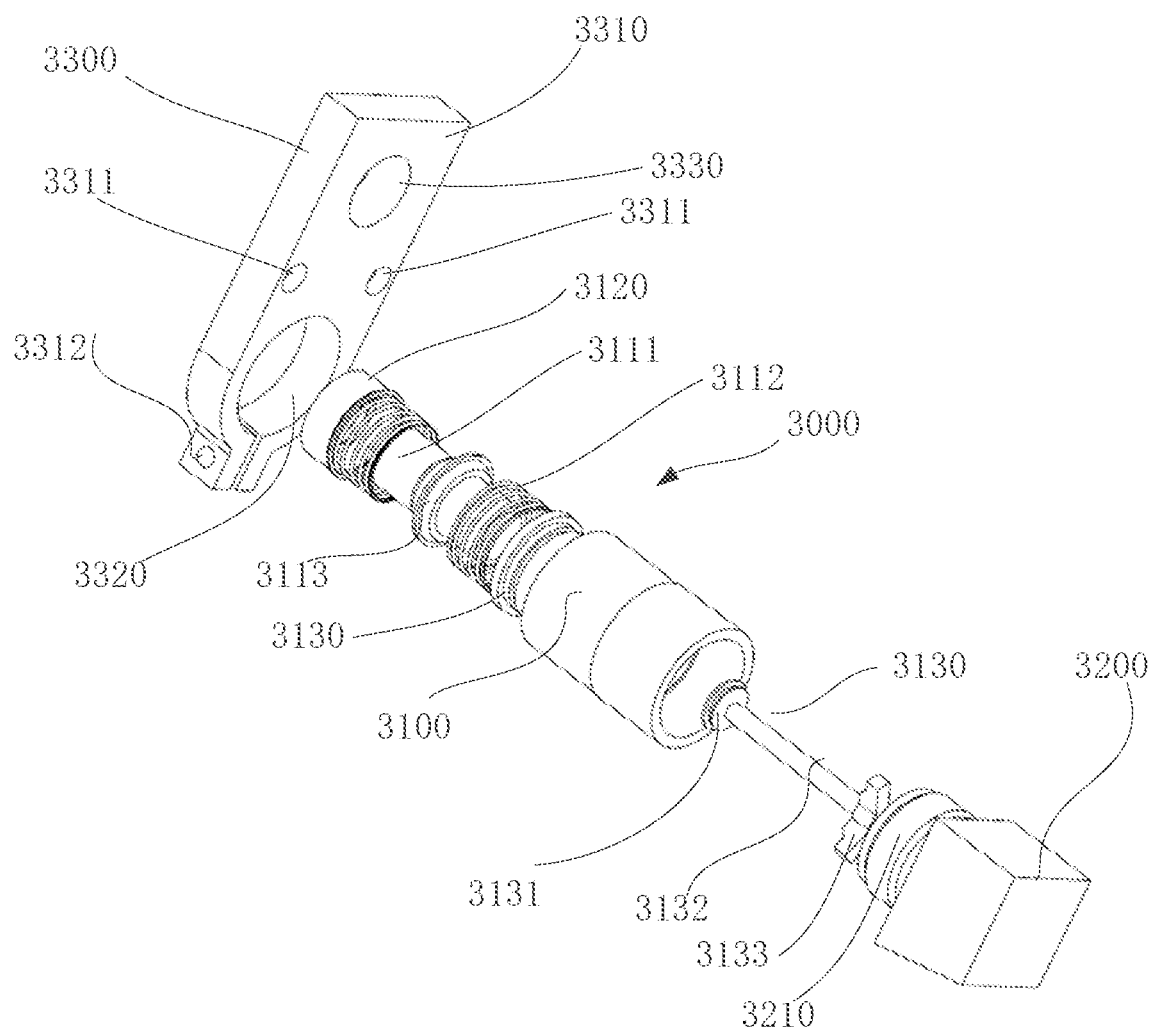
FIG. 15 is a view from another angle illustrating the parts of an embodiment of a mounting base according to the present disclosure.
Figure 16:
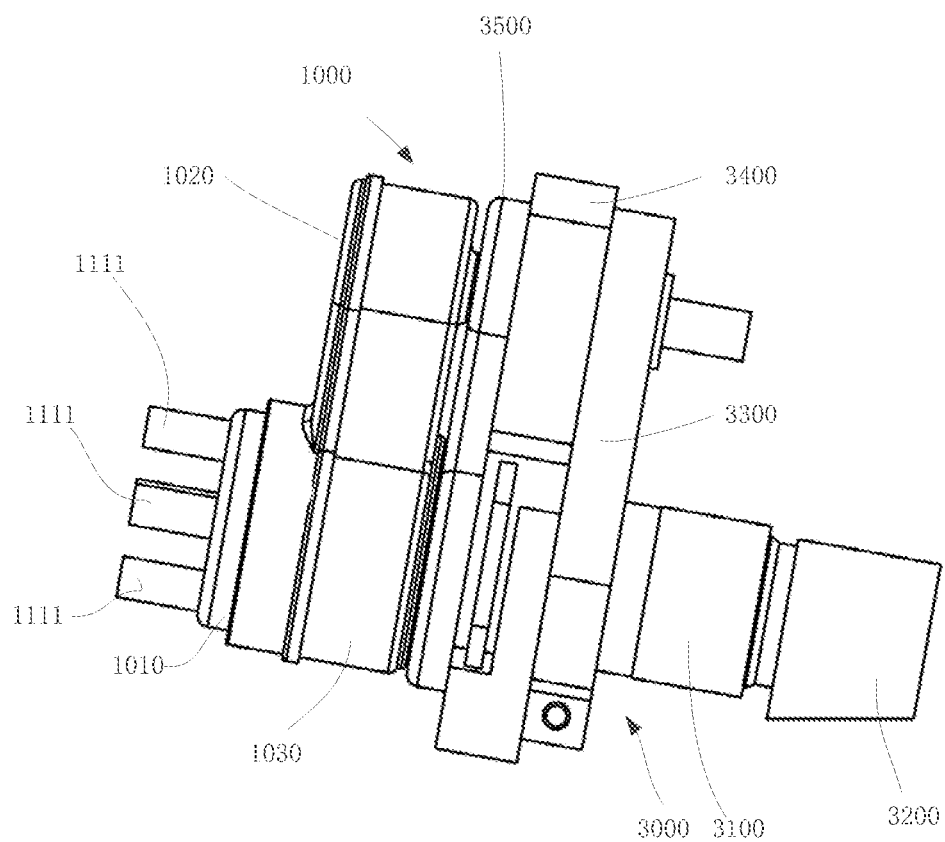
FIG. 16 is a structural view illustrating a manifold and a mounting base being in a mounted state according to the present disclosure.

Referring to FIGS. 14-16, the ejector rod 3130 includes a fixed base 3133 fixed to the internal cavity 3103 of the base, a sealing top 3131 docked with the manifold end docking valve 1201, and an intermediate rod 3132 connected to the fixed base 3133 and the sealing top 3131. Among them, the intermediate rod 3132 and the fixed base 3133, and the intermediate rod 3132 and the sealing top 3131 may all be detachably connected, such as plug-in connection, snap connection, screw connection, etc.

Figure 17:
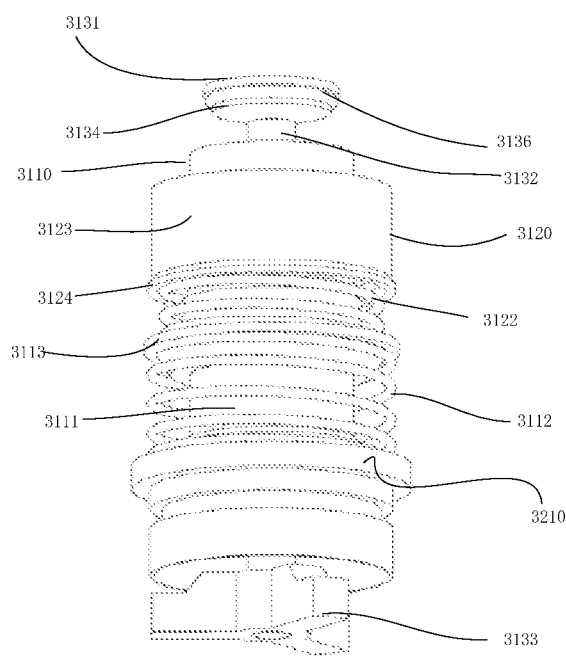
FIG. 17 is a structural view illustrating the parts inside the base housing of an embodiment of a mounting base according to the present disclosure.
Figure 18:
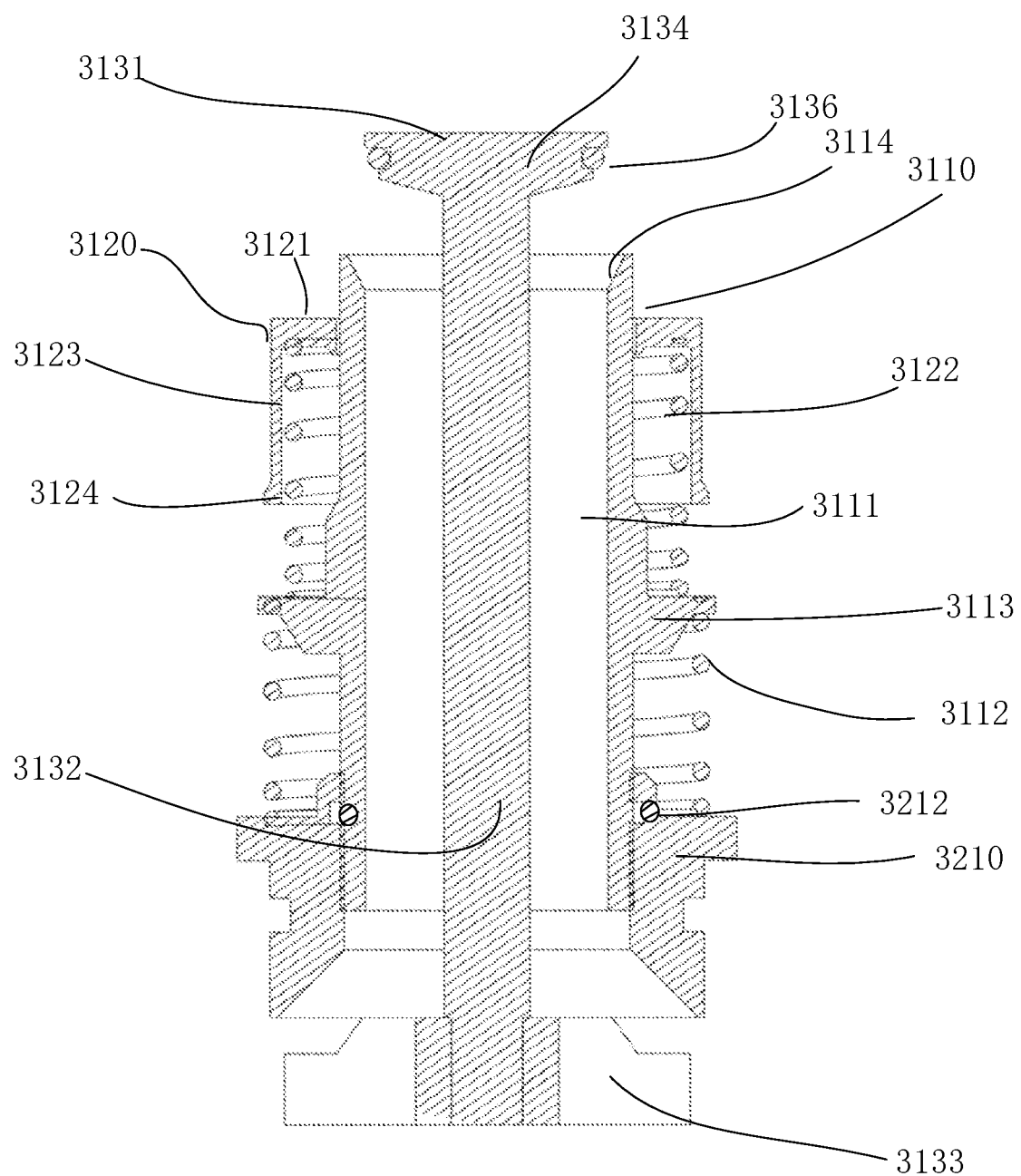
FIG. 18 is a cross-sectional view of the parts inside the base housing of an embodiment of a mounting base according to the present disclosure.

Referring to FIGS. 17 and 18, the sealing top 3131 includes a sealing circular platform 3134 having a top surface facing toward the mounting inlet 3102 and a bottom surface facing toward the internal cavity 3103 of the base, and the diameter of the top surface is larger than the diameter of the bottom surface. Correspondingly, the floating sleeve 3110 is provided with an inclined inner lip 3114 to be mated with the sealing circular platform 3134. The inclined inner lip 3114 is disposed at the port of the floating sleeve 3110 facing toward the mounting inlet 3102, and the inclined inner lip 3114 just mates with the sealing circular platform 3134 so that the port of the floating sleeve 3110 facing toward the mounting inlet 3102 is sealed by the sealing circular platform 3134.

Referring to FIGS. 14-20, a first sealing ring 3136 is provided on the side of the sealing circular platform 3134. Specifically, the first sealing ring 3136 is embedded in an annular groove 3135 formed in the side of the sealing circular platform 3134, and a better seal effect on the sealing circular platform 3134 sealing the port of the floating sleeve 3110 facing toward the mounting inlet 3102 can be achieved by using the first sealing ring 3136.

Referring to FIGS. 14-15, the floating sleeve 3110 specifically includes a floatable tube body 3111, and a second elastic member 3112 connected to the floatable tube body 3111. The second elastic member 3112 can make the floatable tube body 3111 move from the fourth position to the third position, and the second elastic member 3112 is preferably a spring sleeved outside the floatable tube body 3111. In addition, a flexible sleeve material or otherwise any elastic structure capable of providing a rebound force may be also used. The floating sleeve 3110 also includes a locking portion 3113 capable of applying pressure to one end of the second elastic member 3112. The locking portion 3113 can apply pressure to the second elastic member 3112 under the action of an external thrust, and when the external thrust disappears, the second elastic member 3112 can push the locking portion 3113 to return the floatable tube 3111 to the fourth position. An intracavitary tube base 3210 for mating with the floating sleeve 3110 is also provided in the internal cavity 3103 of the base, and the intracavitary tube base 3210 is used for mating with the floating sleeve 3110 when the floating sleeve 3110 is in the third position. At the same time, the intracavitary tube base 3210 can also limit the other end of the second elastic member 3112. When the mounting connector 1210 is inserted, the floating sleeve 3110 is pushed by the mounting connector 1210 and thus applies pressure to the second elastic member 3112 through the locking portion 3113 on the floating sleeve 3110. Meanwhile, one end of the floatable tube body 3111 is coupled with the mounting connector 1210 to form a sealed connection and the other end of floatable tube body 3111 is coupled with the intracavitary tube base 3210 to form a sealed connection.

Figure 19:
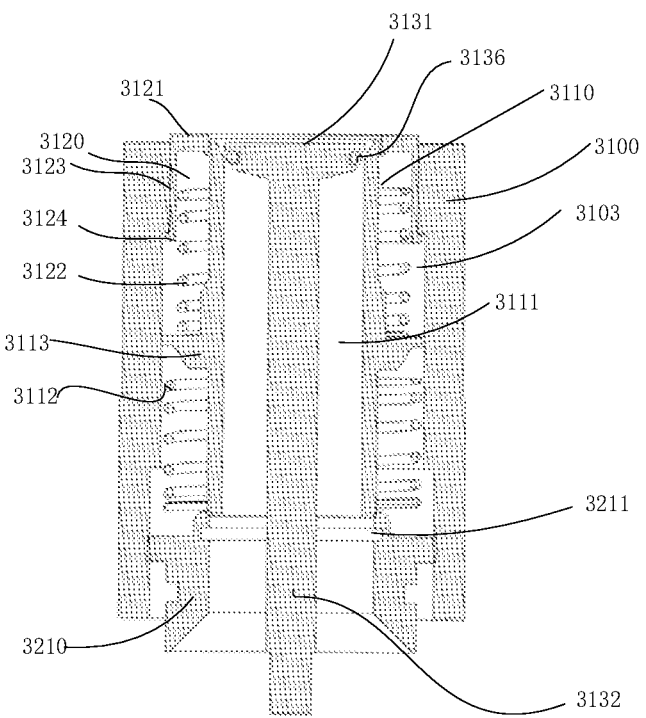
FIG. 19 is a cross-sectional view of the base housing and its internal parts of an embodiment of a mounting base according to the present disclosure.

Referring to FIGS. 16-19, the base end docking valve 3101 further includes a floating seal 3120 sleeved outside the floating sleeve 3110 and positioned in the base housing 3100. Specifically, the floating seal 3120 is sleeved on the portion facing toward the mounting inlet 3102 of the floatable tube body 3111, and the floating seal in this embodiment is disposed to be movable relative to the outer wall of the floatable tube body 3111. Referring to FIG. 19, in this embodiment, when the manifold 1000 is not mounted, the inclined inner lip 3114 is just mated with the sealing circular platform 3134 to form a seal of the sealing circular platform 3134 to the port of the floating sleeve 3110 facing toward the mounting inlet 3102. At this time, the floating seal 3120 closes the gap between the port of the floating sleeve 3110 facing toward the mounting inlet 3102 and the base housing 3100 to form a sealed connection.

Referring to FIGS. 17 and 18, the floating seal 3120 includes a floating sealing panel 3121, and a third elastic member 3122 that moves the floating sealing panel 3121 from a fifth position to a sixth position. The floating seal 3120 further includes a sleeved wall 3123 having an upper end coupled with the floating sealing panel 3121, and the third elastic member 3122 is positioned in the sleeved wall 3123. A sealing ring 3124 is positioned at the lower end of the sleeved wall 3123. The locking portion 3113 of the floating sleeve 3110 is now used as a spacer member for separating the second elastic member 3112 from the third elastic member 3122.

Referring to FIG. 11 and FIG. 18, when the mounting connector 1210 is inserted into the mounting inlet 3102, the sealing top 3131 of the ejector rod 3130 is coupled with the piston base 1231 of the manifold end docking valve 1201, and during the insertion of the mounting connector 1210, the sealing piston 1230 is pushed by the ejector rod 3130 to the first position and the first elastic member 1240 is therefore elastically deformed. At the same time, the floating seal 3120 is pushed by the mounting connector 1210 to move to the fifth position and the third elastic member 3122 is therefore elastically deformed. During this process, the floating seal 3120 simultaneously drives the floatable tube body 3111 to finally move to the third position and elastically deforms the second elastic member 3112. At this time, a gap is formed between the sealing piston 1230 and the second cavity 1212 or the third cavity 1213 to open the connector cavity 1202, and fluid can enter in the mounting connector 1210 through the gap inside the storage connection portion 1200 and the connector cavity 1202. After the floatable tube body 3111 is moved to the third position, the floatable tube body 3111 is separated from the sealing top 3131, and one port of the floatable tube body 3111 is inserted into the connector cavity 1202 of the mounting connector 1210 to form a sealed fluid passage, the other port of the floatable tube body 3111 is inserted into the intracavitary tube base 3210 to form a sealed fluid passage. At this time, the manifold 1000 and the waste collection container 2100 form a passage in fluid communication with each other.

Referring to FIG. 9, FIG. 13 and FIG. 18, when the mounting connector 1210 is detached from the mounting inlet 3102, the first elastic member 1240 pulls the sealing piston 1230 back to the second position, so that the sealing piston 1230 and the connector sealing ring 1244 are coupled to seal the connector cavity 1202. After the mounting connector 1210 is detached, its thrust on the floating seal 3120 disappears, the third elastic member 3122 retracts the floating seal 3120 to the sixth position, and the second elastic member 3112 also retracts the floatable tube body 3111 to the fourth position. The inclined inner lip 3114 is just mated with the sealing circular platform 3134 to form a seal of the sealing circular platform 3134 to the port of the floating sleeve 3110 facing toward the mounting inlet 3102. At this time, the floating seal 3120 closes the gap between the port of the floating sleeve 3110 facing toward the mounting inlet 3102 and the base housing 3100 to form a sealed connection. That is, after the mounting connector 1210 is detached, the floating seal 3120 returns to the sixth position and the floating sleeve 3110 returns to the fourth position so that the base end docking valve 3101 is closed.

Figure 20:
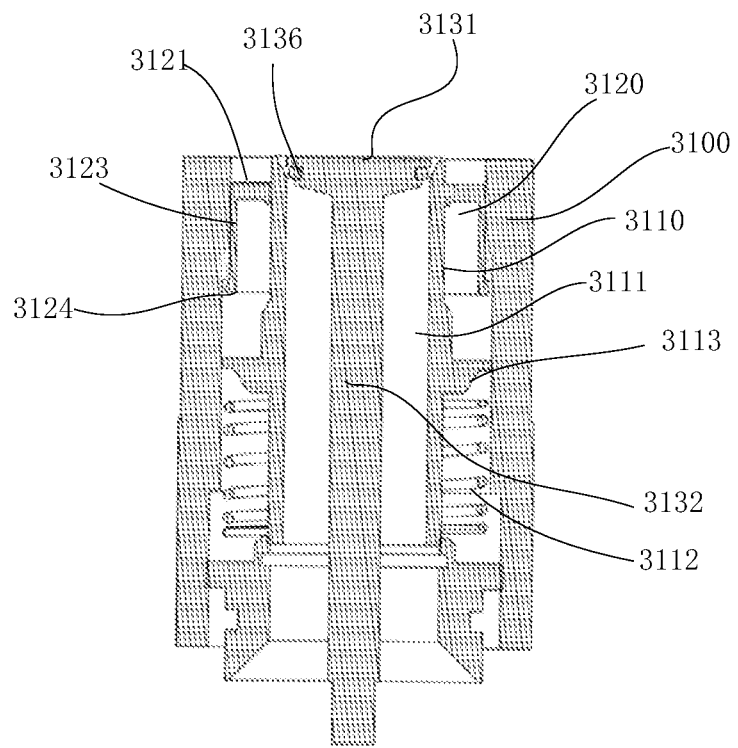
FIG. 20 is a cross-sectional view of the base housing and its internal parts of another embodiment of a mounting base according to the present disclosure.

Referring to FIG. 20, in the embodiment shown in FIG. 20, the floating seal 3120 can be fixed on the outer wall of the floatable tube body 3111, and the floating sealing panel 3121 is positioned below an opening plane in which the floatable tube body 3111 has a tube opening. The distance from the floating sealing panel 3121 to the opening plane of the floatable tube body 3111 is the length of the floatable tube body 3111 being inserted into the connector cavity 1202 after the mounting connector 1210 is inserted. In this embodiment, the floating seal 3210 and the floatable tube body 3111 are integrally formed, so there is no need to add a third elastic member. The second elastic member 3112 may be placed in the position as shown in FIG. 19 and FIG. 20, and the locking portion 3113 may be removed, by which the second elastic member 3112 is arranged between the floating seal panel 3121 of the floating seal 3210 and the intracavitary tube base 3210.

Referring to FIGS. 13-17, the mounting base 3000 further includes a first holder 3300 for locking the base housing 3100. The first holder 3300 is provided with a first bottom plate 3310, a first locking hole 3320 disposed on the first bottom plate 3310 and sleeved on the base housing 3100, and a second locking hole 3330 for mounting other connectors. The first bottom plate 3310 also has a mounting hole 3311 and an elastic hole 3312 for mounting an elastic member. The mounting base 3300 further includes a second holder 3400 for locking the mounting connector 1210 of the manifold 1000. The mounting base 3000 also includes a guide socket 3500 for guiding the mounting connector 1210 of the manifold 1000. When the second holder 3400 is provided, the guide socket 3500 is disposed on the surface of the second holder 3400, and when the second holder 3400 is not provided, the guide socket 3500 is disposed on the surface of the first holder 3300. The guide socket 3500 can also be used as a vacuum mounting base for connecting with the vacuum connection portion 1300 of the manifold 1000, so that a connection path for air flow is formed between the vacuum connection portion 1300 and the vacuum source 2200. The waste collection container 2100 is connected to the vacuum connection portion 1300 in an airflow path manner so that the vacuum source 2200 can provide a suction force for the waste collection container 2100.

The following beneficial effects by implementing the embodiments of the present disclosure can be provided:

First, in the embodiments of the present invention, a vacuum connection portion is added in a manifold so that a vacuum source does not need to be directly connected to a waste collection container, thereby avoiding any complex connection structure being arranged between the waste collection container and the vacuum source, and providing easy detachment and maintenance for both the vacuum source and the waste collection container. Secondly, the waste collection container and the vacuum source can be effectively separated by the manifold after the manifold is placed, thereby reducing the risk of waste pollution to devices. Moreover, the manifold is a disposable component so that the waste in the waste collection container is hard to directly contact the vacuum source regardless of whether the manifold is in use or not, thereby effectively reducing the risk of waste contaminating the device. Next, the manifold can be designed without an additional sealing cover, and thus a sealing cover does not need to be manually opened to mount the manifold to the medical waste collection apparatus in use, while a passageway is automatically formed at the time of the mounting. And meanwhile the manifold can automatically seal its port for connecting with the medical waste collection apparatus after the manifold is taken out, and the medical waste collection apparatus can also automatically seal its port for connection with the manifold, thereby avoiding waste pollution to the environment, equipment and personnel. In addition, the manifold according to an embodiment can be directly inserted into the medical waste collection apparatus during installation without manually opening a sealing cover in advance, and there is also no need to open a seal member at the apparatus end and manually seal the ports for connecting the manifold and the medical waste collection apparatus after use, thereby making operations easier and providing improved convenience of use.

The above disclosure has been described with a preferred embodiment according to the present invention and it cannot be used to limit the scope of the present invention. Therefore, it is understood that equivalent changes and modifications made according to the claims of the present invention still fall within the scope of the present invention.

We claim:

1. A manifold applied to a medical waste collection apparatus, comprising:
   a fluid path connection portion;
   a storage connection portion, wherein the storage connection portion includes:
   a mounting connector, configured to be in communication with the fluid path connection portion and coupled with the mounting base of the medical waste collection apparatus, wherein the mounting connector includes a connector cavity defined by inner walls of the mounting connector; and
   a manifold end docking valve arranged inside the connector cavity,
   wherein the manifold end docking valve is in an open state when the mounting connector is coupled with the mounting base, and a passage is formed between the storage connection portion and a waste collection container disposed in the medical waste collection apparatus;
   wherein the manifold end docking valve is in a closed state to close the connector cavity when the mounting connector is detached from the mounting base;
   wherein the manifold end docking valve includes a sealing piston and a first elastic member, and the connector cavity includes a first cavity and a second cavity;
   wherein the sealing piston is movable between a first position and a second position;
   wherein when the mounting connector is connected to the mounting base, the sealing piston is in the first position so that the sealing piston enters the second cavity, and a passage is formed between the storage connection portion and the waste collection container in the medical waste collection apparatus;
   wherein when the mounting connector is detached from the mounting base, the sealing piston is in the second position so that the sealing piston returns to the first cavity and seals the connector cavity;
   wherein the first elastic member cooperates with the sealing piston to make the sealing piston rebound from the first position to the second position;
   wherein the sealing piston includes a piston base and a piston rod disposed on the piston base;
   wherein a guide tube for accommodating the movement of the piston rod is disposed in the mounting connector;
   wherein the first elastic member is a spring; and
   wherein the spring is sleeved on the guide tube and the piston rod.

2. The manifold according to claim 1, wherein a connector sealing ring is disposed between the piston base and the connector cavity so that the connector sealing ring is mated with the sealing piston to seal the connector cavity when the sealing piston is in the second position.

3. The manifold according to claim 2, wherein the connector sealing ring is positioned in an inner sealing groove, the inner sealing groove is disposed on the piston base or in an inner wall of the connector cavity.

4. The manifold according to claim 1, wherein the inner diameter of the second cavity is greater than the inner diameter of the first cavity.

5. The manifold according to claim 1, wherein a filtering bin is disposed between the fluid path connection portion and the storage connection portion.

6. The manifold according to claim 5, wherein a filter screen is positioned in the filtering bin.

7. The manifold according to claim 6, wherein the guide tube is disposed on the filter screen.

8. The manifold according to claim 1, wherein the mounting connector further includes a sleeve head sleeved on the first cavity.

9. The manifold according to claim 8, wherein a connector sealing ring is positioned in the sleeve head.

10. The manifold according to claim 8, wherein the sleeve head is further provided with a mounting sleeve groove that can be coupled with the outer wall of the first cavity.

11. The manifold according to claim 1, wherein the connector cavity further includes a third cavity having an inner diameter greater than the inner diameter of the second cavity.

12. The manifold according to claim 1, wherein the manifold further includes a vacuum connection portion for connecting to the vacuum source in an airflow path manner, and meanwhile the vacuum connection portion is also connected to the waste collection container in an airflow path manner, such that a suction force can be provided for the waste collection container.

* * * * *